United States Patent [19]

Allison et al.

[11] Patent Number: 4,935,343

[45] Date of Patent: Jun. 19, 1990

[54] MONOCLONAL ANTIBODIES FOR INTERLEUKIN-1β

[75] Inventors: Anthony C. Allison; Elsie M. Eugui, both of Belmont; John S. Kenney, Palo Alto; Marvin P. Masada, Mountain View, all of Calif.

[73] Assignee: Syntex (U.S.A.) Inc., Palo Alto, Calif.

[21] Appl. No.: 895,003

[22] Filed: Aug. 8, 1986

[51] Int. Cl.$^5$ .................................. G01N 33/53
[52] U.S. Cl. ..................... 435/7; 435/70.21; 435/172.2; 435/240.27; 435/810; 436/501; 436/512; 436/518; 436/548; 436/808; 424/85.1; 424/85.2; 530/351; 530/387
[58] Field of Search ............... 435/7, 68, 810, 240.27, 435/172.2; 436/501, 512, 548, 518, 808; 424/88, 85; 530/387, 808, 809, 806

[56] References Cited

U.S. PATENT DOCUMENTS

| | | | |
|---|---|---|---|
| 4,134,792 | 1/1979 | Boguslaski et al. | 435/7 |
| 4,376,110 | 3/1983 | David et al. | 436/513 |
| 4,444,887 | 4/1984 | Hoffmann | 435/240 |

OTHER PUBLICATIONS

Kenney et al., Journal of Immunology, vol. 138, No. 12, pp. 4236–4242, Jun. 1987.

Kohler et al., Nature, vol. 256 (Aug. 1975) pp. 495–497.

March et al., "Cloning, Sequence and Expression of Two Distinct Human Interleukin–1 Complementary DNAs", *Nature*, vol. 315, Jun. 20, 1985, pp. 641–647.

Gubler et al., "Recombinant Human Interleukin 1α: Purification and Biological Characterization", *J. Immun.*, vol. 136, No. 7, Apr. 1, 1986, pp. 2492–2497.

Ehrlich et al., "Mixing Two Monoclonal Antibodies Yields Enhanced Affinity for Antigen", *J. Immun.*, vol. 128, No. 6, Jun. 1982, pp. 2709–2713.

Köck et al., "Characterization of a Monoclonal Antibody Directed Against the Biologically Active Site of Human Interleukin 1", *J. Exp. Med.*, vol. 163, Feb. 1986, pp. 463–468.

*Primary Examiner*—Robert J. Warden
*Assistant Examiner*—Carol A. Spiegel
*Attorney, Agent, or Firm*—Linda J. Nyari; Theodore J. Leitereg

[57] ABSTRACT

The present invention is concerned with novel monoclonal antibodies which bind to Interleukin-1β and do not bind to Interleukin-1β. The antibodies bind to Interleukin-1β and block receptor binding and biological activity. The antibodies find use in, for example, diagnostic methods such as an assay for the detection of Interleukin-1β.

18 Claims, 6 Drawing Sheets

MONOCLONAL ANTIBODIES FOR INTERLEUKIN-1β

BACKGROUND OF THE INVENTION

1. Field of the Invention

Various types of protein mediators (lymphokines) are produced when lymphocytes and monocytes undergo blast transformation from stimulation by, for instance, antigens, antibodies against surface components of the lymphocyte or certain plant mitogens. Two such lymphokines, Interleukin 1 (IL-1) and Interleukin 2 (IL-2), are known to modulate T and B cell immune responses in mammals, including: (1) enhancement of thymocyte mitrogensis; (2) induction of alloantigen specific cytotoxic T cell reactivity; and (3) assistance in the generation of helper T cells in antibody responses following stimulation with heterologous erythrocytes. In addition, IL-2 is capable both of sustaining the in vitro exponential proliferation of effector T cells lines and of inducing in vitro and vivo generation of cytotoxic T cells from nude mouse spleens.

Lymphokines like IL-1 are of multicellular origin, and through their multifaceted regulatory actions they affect a variety of different target cells during host response to infections. IL-1 at the site of inflammation activates lymphocytes, granulocytes, and fibroblasts. Moreover, IL-1 also may act as mediator of the acute-phase response, promote catabolism of structural protein and matrix and regulate the febrile response. To further elucidate these multiple biological effects on different tissues and to investigate whether they are regulated by a single family of related molecules, it is necessary to analyze the sequence of the IL-1 molecule and to develope antibodies directed against IL-1.

Two proteins that share human Interleukin-1(IL-1) activity but are structurally distinct molecules have been identified. These proteins, termed IL-1α and IL-1β, compete with one another for binding to IL-1 receptors and mediate similar biological activities. Both molecules are synthesized as large precursors ($M_r$s~30,000) that are processed to smaller biologically active forms ($M_r$s~17,500). However, they are encoded by two distinct complementary DNAs, show only a 26% amino acid homology, and have pI's (isoelectric pH's) of 5 and 7, respectively.

2. Description of the Related Art

The characterization of a monoclonal antibody directed against the biologically active site of human Interleukin-1 is discussed by Köck et al (1986) *J. Exp. Med.*, 163: 463–468. A hybridoma antibody which inhibits Interleukin 2 activity is disclosed in U.S. Pat. Nos. 4,411,993 and 4,473,493. A process for making human antibody producing B-lymphocytes in described in U.S. Pat. No. 4,444,887. The cloning, sequence, and expression of two distinct human Interleukin-1 complimentary DNAs is discussed by March et al. (1985) *Nature*, 315: 641–647.

SUMMARY OF THE INVENTION

The present invention is concerned with novel monoclonal antibodies which bind to Interleukin-1β ("IL-1β") and do not bind to Interleukin-1α ("IL-1α"). The antibodies bind to IL-1β and block receptor binding to, and biological activity of, IL-1β.

The invention also concerns certain diagnostic methods employing the monoclonal antibodies of the invention. One such method involves the determination of the presence of IL-1β in a sample suspected of containing IL-1β. The sample is contacted with a monoclonal antibody of the invention. The contact is carried out under conditions for binding of the antibody to IL-1β. After contact, the presence or absence of binding of the antibody to IL-1β in the sample is determined. This binding is related to the presence or absence of IL-1β in the sample.

DESCRIPTION OF THE SPECIFIC EMBODIMENTS

Figure 1:
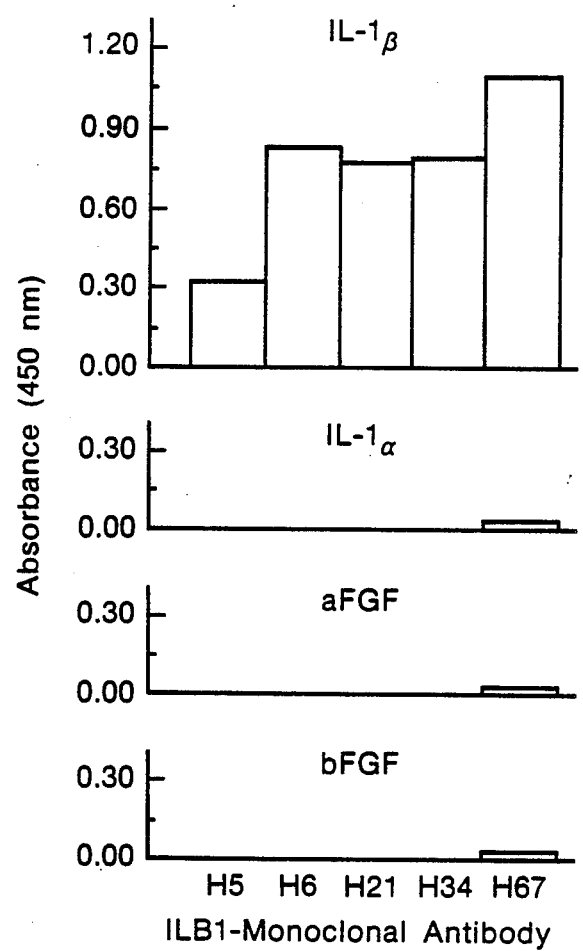
FIG. 1 shows results indicating that the monoclonal antibodies of the invention are specific for IL-1β and do not bind IL-1β or homologous growth factors.

The present invention concerns certain novel antibodies specific for a determinant site on IL-1β and certain diagnostic methods employing such antibodies. The monoclonal antibodies of the invention can be produced according to the standard techniques of Köhler and Milstein (1975) *Nature*, 256: 495–497. For example, IL-1β purified by known techniques or genetically engineered by recombinant DNA technology is used as the immunogen. This immunogen is injected into a mouse and, after a sufficient time, the mouse is sacrificed and spleen cells obtained, The spleen cell chromosomes encoding desired immunoglobulins are immortalized by fusing the spleen cells with myeloma cells or with lymphoma cells, generally in the presence of polyethylene glycol. The resulting cells, which include the hybrid continuous cell lines (hybridomas) are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. When an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Köhler and Milstein, supra).

One such monoclonal antibody of the present invention is exemplified by a novel antibody designated ILB1-H6. This monoclonal antibody defines a determinant site on the IL-1β molecule that is involved in receptor binding and proliferative activity of IL-1β. This antibody does not bind to IL-1α and does not bind to acidic or basic fibroblast growth factors. By the term "does not bind" is meant that no significant binding above background is observed when the antibody is combined with IL-1α or with the fibroblast growth factors. Antibody ILB1-H6 blocks the binding of iodine 125 labeled IL-1β to IL-1 receptors on mouse 3T3 fibroblasts and IL-1β-induced thymocyte proliferation. Antibody ILB1-H6 is of the IgG1κ isotype. The ILB1-H6 antibody is produced by the ILB1-H6 murine hybridoma.

Another monoclonal antibody of the invention is designated ILB1-H21 and defines a determinant site on the IL-1β molecule that is involved in receptor binding and proliferative activity of IL-1β. This antibody does not bind to Il-1α and does not bind to acidic or basic fibroblast growth factors. Antibody ILB1-H21 blocks the binding of iodine 125 labeled IL-1α to IL-1 receptors on mouse 3T3 fibroblasts and IL-1β-induced thymocyte proliferation. This antibody is of the IgG1κ isotype. The ILB1-H21 antibody is produced by the ILB1-H21 murine hybridoma.

Another monoclonal antibody of the invention is designated ILB1-H34 and defines a determinant site on the IL-1β molecule that is involved in receptor binding and proliferative activity of IL-1β. This antibody does not bind to IL-1α and does not bind to acidic or basic fibroblast growth factors. Antibody ILB1-H34 blocks the binding of iodine 125 labeled IL-1β to IL-1 receptors on mouse 3T3 fibroblasts and IL-1β-induced thymocyte proliferation. This antibody is of the IgG1κ isotype. The HLB1-H34 antibody is produced by the ILB1-H34 murine hybridoma.

Another monoclonal antibody of the invention is designated ILB1-H67 and defines a determinant site on the IL-1β molecule that is involved in receptor binding and proliferative activity of IL-1β. This antibody does not bind to IL-1α and does not bind to acidic or basic fibroblast growth factors. Antibody ILB1-H67 blocks the binding of iodine 125 labeled IL-1β to IL-1 receptors on mouse 3T3 fibroblasts and IL-1β-induced thymocyte proliferation. This antibody is of the IgG2bκ isotype and is produced by the ILB1-H67 murine hybridoma.

Also included within the scope of the invention are useful binding fragments of the monoclonal antibodies above such as Fab, F(ab')2, Fc fragments and so forth. The antibody fragments are obtained by conventional techniques. For example, useful binding fragments may be prepared by peptidase digestion of the antibody using papain or pepsin.

While the above specific examples of the novel antibodies of the invention are directed to antibodies binding to specific determinant sites and being of specific classes and isotypes from a murine source, this is not meant to be a limitation. The above antibodies and those antibodies having functional equivalency with the above antibodies, whether from a murine source, mammalian source including human, or other sources, or combinations thereof are included within the scope of this invention, as well as other classes such as IgM, IgA, IgE, and the like, including isotypes within such classes. By the term "functional equivalency" is meant that the antibody is capable of binding to the IL-1β molecule but not to the IL-1α molecule and is capable of competing with a particular antibody of the invention for such site. That is, such antibody, when combined with IL-1β, or a fragment having a determinant site common with IL-1β, will bind to such determinant site and will block an antibody of the invention from binding to such site. Furthermore, since the IL-1β molecule can have more than one determinant site, the invention includes monoclonal antibodies which define determinant sites on IL-1β other than determinant sites defined by the aforementioned monoclonal antibodies.

Competition studies suggest that two non-overlapping determinant sites or epitopes on the IL-16 molecule are recognized by monoclonal antibodies ILB1-H6, -H21, -H34, and -H67. Antibodies ILB1-H6 and -H34 recognize one epitope and antibodies ILB1-H21 and -H67 recognize another. Thus, two epitopes that are involved in receptor-binding and proliferative activity of IL-1β are recognized.

The antibodies of the present invention find use in diagnostic assays for the determination of IL-1β. The antibodies of the invention may be used in most assays involving antigen-antibody reactions. The assays may be homogeneous or heterogeneous. In a homogeneous assay approach, the sample can be a biological fluid such as serum, urine, whole blood, lymphatic fluid, plasma, saliva, and the like, cells, tissue, and material secreted by cells or tissues cultured in vitro. The sample can be pretreated if necessary to remove unwanted materials. The immunological reaction usually involves the specific antibody, labeled analyte, and the sample suspected of containing the analyte. The analyte can be directly labeled with the label or indirectly labeled with a means for incorporating the label such as conjugation of the analyte to biotin and having labeled avidin or anti-biotin. The signal from the label is modified, directly or indirectly, upon the binding of the antibody of the labeled analyte. Both the immunological reaction and detection of the extent thereof are carried out in a homogeneous solution. Labels which may be employed as part of a signal producing system capable of producing a signal in relation to the amount of analyte in the sample include free radicals, chromogens, such as fluorescent dyes, chemiluminescers, enzymes, bacteriophages, coenzymes particulate labels and so forth.

In a heterogeneous assay approach, the reagents are usually the sample, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal or signal producing system. The signal is related to the presence of the analyte in the sample. Means for producing a detectable signal includes the use of radioactive labels, fluorescers, enzymes, and so forth. Exempary of heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

One embodiment of an assay employing an antibody of the present invention involves the use of a surface to which the monoclonal antibody of the invention is attached. The underlying structure of the surface may take different forms, have different compositions and may be a mixture of compositions or laminates or combinations thereof. The surface may assume a variety of shapes and forms and may have varied dimensions, depending on the manner of use and measurement. Illustrative surfaces may be pads, beads, discs, or strips which may be flat, concave or convex. Thickness is not critical, generally being from about 0.1 to 2 mm thick and of any convenient diameter or other dimensions. The surface typically will be supported on a rod, tube, capillary, fiber, strip, disc, plate, cuvette and the like. The surface will typically be porous and polyfunctional or capable of being polyfunctionalized so as to permit covalent binding of the monoclonal antibody of the invention as well as to permit bonding of other compounds which form a part of a means for producing a detectable signal.

A wide variety of organic and inorganic polymers, both natural and synthetic, and combinations thereof, may be employed as the material for the solid surface. Illustrative polymers include polyethylene, polypropylene, poly(4-methylbutene), polystyrene, polymethracrylate, poly(ethylene terephthalate), rayon, nylon, poly(vinyl butyrate), silicones, polyformaldehyde, cellulose, cellulose acetate, nitrocellulose, latex, etc. Other materials which may be employed include paper, glasses, ceramics, metals, metalloids, semiconductor materials, cermets, silicates or the like. Also included are substrates that form gels, gelatins, lipopolysaccharides, silicates, agarose and polyacrylamides or polymers which form several aqeuous phases such as dextrans, polyalkylene glycols (alkylene of 2 to 3 carbon atoms) or surfactants such as phospholipids.

The binding of the monoclonal antibody of the invention to the surface may be accomplished by well known techniques, commonly available in the literature. See, for example, "Immobilized Enzymes," Ichiro Chibata, Halstad Press, New York (1978) and Cuatrecasas, *J. Bio. Chem.*, 245: 3059 (1970).

In carrying out the assay in accordance with this embodiment of the invention the sample is mixed with an aqueous medium and the medium is contacted with the surface having a monoclonal antibody of the invention bound thereto. Members of a signal producing system and any ancillary materials may also be included in the aqueous medium, either concurrently or added subsequently so as to provide a detectable signal associated with the surface. The means for producing the detectable signal can involve the incorporation in the medium of a labeled analyte or it may involve the use of a second monoclonal antibody having a label conjugated thereto. Separation and washing steps will be carried out as needed. The signal detected is related to the presence of IL-1β in the sample. It is within the scope of the present invention to include a calibration as well as the measurement surface on the same support.

A particular embodiment of an assay in accordance with the present invention, by way of illustration and not limitation, involves the use of a support such as a slide or a well of a petri dish. The technique involves fixing the sample to be analyzed on the support with an appropriate fixing material such as acetone and incubating the sample on the slide with a monoclonal antibody of the invention. After washing with an appropriate buffer such as, for example, phosphate buffered saline, the support is contacted with a labeled specific binding partner for the analyte in the sample. After incubation as desired, the slide is washed a second time with an aqueous buffer and the determination is made of the binding of the labeled monoclonal antibody to the analyte. If the label is fluorescent, the slide may be covered with a fluorescent antibody mounting fluid on a cover slip and then examined with a fluorescent microscope to determine the extent of binding. On the other hand, the label can be an enzyme conjugated to the monoclonal antibody of the invention and the the extent of binding can be determined by examining the slide for the presence of enzyme activity, which may be indicated by the formation of a precipitate, a color, or the like.

For an expanded discussion of the various general techniques discussed above with regard to conducting an assay on a surface see U.S. Pat. Nos. 4,299,916; 4,391904; 4,533,629; and 4,540,659; the disclosures of which are incorporated herein by reference in their entirety.

A particular example of an assay utilizing the present antibodies is a double determinant ELISA assay. A support such as, e.g., a glass or vinyl plate, is coated with antibody ILB1-H6 by conventional techniques. The support is contacted with the sample suspected of containing IL-1β, usually in a aqueous medium. After an incubation period from 30 seconds to 12 hours, the support is separated from the medium, washed to remove unbound IL-1β with, for example, water or an aqueous buffered medium, and contacted with, e.g., antibody ILB1-H67, again usually in an aqueous medium. The ILB1-H67 is labeled with an enzyme directly or indirectly such as, e.g., horseradish peroxidase or alkaline phosphatase. After incubation, the support is separated from the medium, and washed as above. The enzyme activity of the support or the aqueous medium is determined. This enzyme activity is related to the amount of IL-1B in the sample.

The antibodies of the invention can also be employed in a conventional immunosorbent purification or affinity chromatography of IL-1β from impure mixtures such as extracts from crude supernatants from normal and genetically engineered cells. Immunosorbent purification is described by James W. Goding in "Monoclonal Antibodies: Principles and Practices," Academic Press, Inc., Orlando, FL (1983). The antibody or fragments thereof are bound to a support which is then contacted with the impure mixture containing IL-1β. The support is washed free of unbound materials with, e.g., buffered saline. Pure IL-1β is recovered from the support by elution such as by contacting the support with, for example, chaotropic agents such as thiocyanide ions, iodine ions, chlorate ions, etc., or by changes in pH.

The invention also includes kits, e.g., diagnostic assay kits, for carrying out the methods disclosed above. In one embodiment, the kit comprises in packaged combination (a) a monoclonal antibody more specifically defined above and (b) a conjugate of a specific binding partner for the above monoclonal antibody and a label capable of producing a detectable signal. The reagents may also include ancillary agents such as buffering agents and protein stabilizing agents, e.g., polysaccharides and the like. The kit may further include, where necessary, other members of the signal producing system of which system the label is a member, agents for reducing background interference in a test, control reagents, apparatus for conducting a test, and the like. In another embodiment, the diagnostic kit comprises a conjugate of monoclonal antibody of the invention and a label capable of producing a detectable signal. Ancillary agents as mentioned above may also be present.

For purification of IL-1β the kit can comprise a support to which a monoclonal antibody of the invention is bound. Furthermore, the kit can include reagents for washing the support free of unbound materials and reagents for removing the bound IL-1β from the support.

The antibodies of the invention may find use therapeutically. Antibodies with proper biological properties are useful directly as therapeutic agents. Alternatively, the antibodies can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68: 317-328).

Another therapeutic use of the monoclonal antibodies of the present invention is the immunization of a patient with an anti-idiotypic antibody raised by using one of the present monoclonal antibodies as an immunogen. Such immunization can induce an active anti-tumor activity (see, for example, Nepom et al.: *Proc. Natl. Acad. Sci. U.S.A.* (1984) 81: 2864-2867.

A particularly attractive aspect of the present invention is that a combination of two or more of the present antibodies can be employed. The combination is effective in binding more than one determinant site on the IL-1β molecule such as those referred to above. For example, monoclonal antibodies ILB1-H6 and -H21 can be combined in effective amounts, i.e., amounts that will render the combination capable of recognizing the above-mentioned two epitopes. Additionally, two of the antibodies of the invention can be employed in an assay method such as, e.g., a double-determinant ELISA assay.

EXAMPLES

The invention is further demonstrated by the following illustrative examples. Parts and percentages are by weight unless otherwise specified.

Materials—BALB/c female mice were obtained from Banting and Kingman (Freemont, CA). Complete and Incomplete Freunds Adjuvant (CFA and IFA) were from Difco (Detroit, MI). HB101 was from Hana Biologics, Inc. (Berkeley, CA). Dulbecco's Phosphate-Buffered Saline (PBS) without calcium and magnesium, and glutamine were from GIBCO Labs (Grand Island, NY). Fetal bovine serum was from Hyclone Labs (Logan, UT) and Hypoxanthine-Aminopterin-Thymidine (HAT) and Hypoxanthine-Thymidine (HT) supplements, and 50% polyethylene glycol (PEG) 1450 were from Bethesda Research Labs (Gaithersburg, MD). Rabbit anti-mouse IgG+A+M peroxidase conjugate, strepavidin peroxidase, mouse Ig isotype identification kit and orthophenylene diamine (OPD) were from Zymed Labs (South San Francisco, CA). Sepharose protein-A and Sephadex G-25 were from Pharmacia (Piscataway, NJ). Pristane (2,6,10,14-tetramethyl pentadecane) was from Aldrich Chem Co. (Milwaukee, WI). [$^{125}$I]Bolton-Hunter reagent was from New England Nuclear (Boston, MA). All other chemicals were analytical grade from Sigma.

Hybridoma Production—Hybridomas to IL-1β were produced using the method of Kohler and Milstein, supra as described by Lerner (1981) *Yale J. Biol. Med.,* 54: 347. Twelve week old female BALB/c mice were injected intraperitoneally and in the hind footpads with 5 μg of purified $M^r$ 17,500 form of IL-1β in CFA. Five booster injections in Incomple Freund's Adjuvant (IFA) were given at 3-4 week intervals. Serum antibody titers were determined periodically by ELISA and after 5 injections a titer was detectable. The animal chosen for fusion received an intravenous (IV) boost of 10 μg of IL-1β in sterile PBS. The spleen was removed 4 days later and the splenocytes fused with P3X63-Ag8.653 Myeloma cells using 50% PEG 1450. Cells were cultured in 96-well plates ($1 \times 10^6$ cells/well) in HAT medium. Hybridoma supernatants were assayed for anti-IL-1β activity by solid-phase antigen ELISA, solid-phase antibody RIA with [$^{125}$I]I1-1β and inhibition of IL-1β-induced thymocyte proliferation (see below). Hybridomas were cloned by limiting dilution in HAT medium with thymocytes ($5 \times 10^5$/well) at least 3 times.

Antibody production and purification—Monoclonal antibody was produced in ascites by injecting $2 \times 10^6$ hybridoma cells intraperitoneally into pristane-treated mice (Köhler et al., supra). Ascites fluid was collected and antibody purified by sepharose-protein A chromatography (Goding (1978) *J. Immunol. Methods,* 20: 241.

Monoclonal antibodies ILB1-H5, -H6, -H21, -H34, and -H67 were prepared from the corresponding cell lines as described above. Monoclonal antibody ILB1-H5 binds to IL-1β and does not bind to IL-1α or to IL-1 receptors to block biological activity.

ELISA of IL-1β antibody—Vinyl assay plates (Costar) were coated with 50 μl/well of a 5 μg/ml solution of antigen diluted in PBS and incubated overnight at 4° C. Wells were countercoated using 5% non-fat dry milk/0.05% Thimerosal/PBS one hour at room temperature. The wells were washed with 0.1% bovine serum albumin (BSA)/0.05% Thimerosal/PBS and 50 μl/well of anti-IL-1β antibodies were incubated for 2 hours at room temperature. Antibody was detected by indirect ELISA using rabbit anti-mouse IgG+A+M peroxidase conjugate and OPD substrate solution. Alternatively, purified monoclonal antibody was biotinylated (Geusdon et al. (1979) *J. Histochem. Cytochem.,* 27: 1131 and detected using strepavidin peroxidase and OPD substrate solution. Isotype of the monoclonal antibodies was identified by indirect ELISA using a mouse Ig isotype identification kit.

Thymocyte proliferation assay—IL-1β and PHA (10 ug/ml) were added to cultures of C3H/HeJ mouse thymocytes ($1 \times 10^6$/well) in MEM/5% fetal bovine serum (FBS)/100 μg/ml gentamicin, 2-mercaptoethanol ($2 \times 10^{-5}$M), 25 mM Hepes medium. After 48 hours at 37° C., 0.5 uCi/well of [$^3$H]thymidine was added and the cultures were incubated overnight. The cells were collected on glass fiber filters using a cell harvester and processed for scintillation counting.

Receptor binding assay—The $M_r \sim 17,500$ form of IL-1β was labeled using diiodo [$^{125}$I]Bolton-Hunter reagent according to the manufacturer's instructions. One μg of Il-1β in 10 μl of PBS was reacted with 1 mCi of reagent for 4 hours at 4° C.; 500 μl of PBS/0.2% gelatin was added and labeled IL-1β was separated from free Bolton-Hunter reagent by chromatography on a $20 \times 1$ cm column of Sephadex G-25 with PBS/0.2% gelatin. [$^{125}$I]IL-1β was added to confluent monolayers of BALB/c 3T3 fibroblasts in DMEM/1% BSA/0.1% sodium azide/0.01% Triton X-100 in 24- well culture plates. After 1 hour at 37° C. the monolayers were washed extensively in media without labelled IL-1β. The monolayers were removed using 0.1N NaOH for gamma counting. Non-specific binding of [$^{125}$I]IL-1β was measured by incubating in the presence of 200-fold molar excess of unlabeled IL-1β.

Determination of antibody affinity—Monoclonal antibody affinity was determined from data obtained using an immunoprecipitation radioimmunoassay. Briefly, 5000 cpm/tube of [$^{125}$I]IL-1β was incubated with dilutions of purified monoclonal antibody in 0.3 ml of 1% non-fat dry milk/0.5% thimerosal/PBS overnight at 4° C. Antigen-antibody complexes were precipitated by the addition of 100 μl/tube each of 10% normal mouse serum/PBS and 4 mg/ml goat anti mouse IgG sera in PBS. After 4 hours at 4° C., the 1/ml tube of ice-cold 2% polyethylene glycol-6000 was added and the tubes centrifuged at 3000×g for 20 min. at 4° C. The supernatants were aspirated and the pellets counted in a gamma counter. Affinity constants were calculated from bound/free ratios at different concentrations of antibody Berson et al. (1968) Clin. Chim. Acta., 22: 51–69.

EXAMPLE 1

Monoclonal antibodies to recombinant IL-1β do not bind IL-1α or homologous growth factors. Monoclonal antibodies were developed to the $M_r$ 17,500 form of recombinant IL-1β as described above. Antibody (100 ng/well) was assayed for specificity by a solid-phase antigen ELISA on polyvinyl chloride microwells coated with a 5 μg/ml (250 ng/well) solution of either IL-1α, IL-1β, acidic or basic Fibroblast Growth Factors (aFGF or bFGF). The amino acid sequence homology of the $M_r$ 17,500 form of IL-1β versus IL-1α, aFGF and bFGF is 23, 27 and 25%, respectively. The results are given in FIG. 1.

EXAMPLE 2

Figure 2:
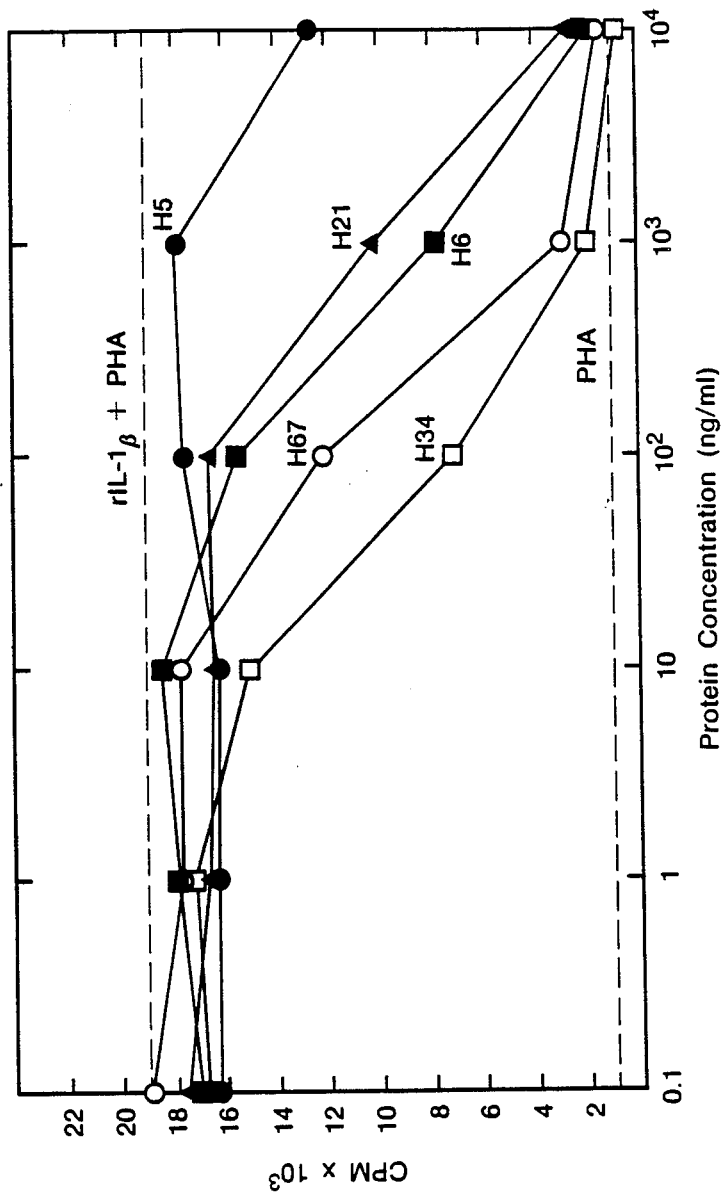
FIG. 2 shows results indicating that the present monoclonal antibodies block IL-1β induced thymocyte proliferation or biological activity of IL-1β.

Monoclonal Antibodies ILB1-H6, H21, H34, and H67 were found to block IL-1β-induced thymocyte proliferation. Monoclonal antibody, IL-1β (1 ng/ml) and PHA (10 μg/ml) were incubated in 100 μl volumes for 1 hr. at 37° C. Mouse C3H/HeJ thymocytes (1×10$^6$/well in 150 μl) were added and cultured for 48 hr at 37° C. Cultures were pulsed overnight with 0.5 μCi/well of [$^3$H]thymidine. The thymocytes were collected onto glass fiber filters using a cell harvester and [$^3$H]thymidine uptake was determined by scintillation counting. ILB1-H5, ●; -H6, ■; -H21, ▲; -H34, □; and -H67, ○. The results are summarized in FIG. 2.

EXAMPLE 3

Figure 3:
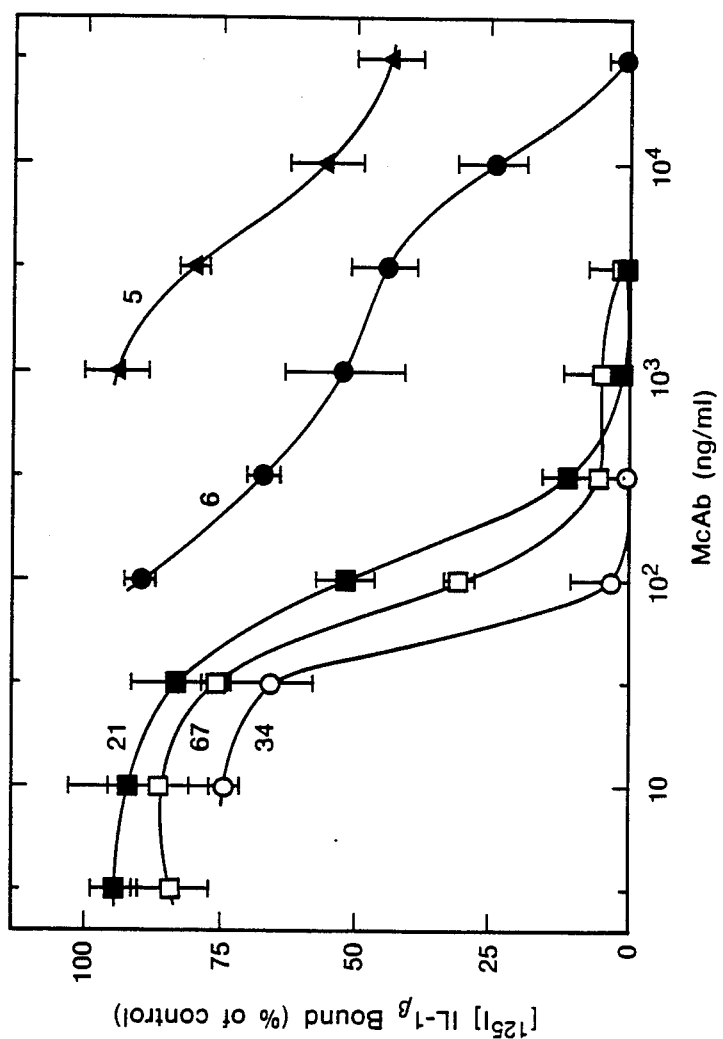
FIG. 3 shows the results indicating that the monoclonal antibodies of the invention block the biological activity of IL-1β to IL-1 by inhibiting the binding of IL-1β to IL-1 receptors.

Monoclonal antibodies ILB1-H6, -H21, -H34, and -H67 block the binding of [$^{125}$I]IL-1β to IL-1β receptors on mouse 3T3 fibroblasts. [$^{125}$I]IL-1β was prepared using [$^{125}$I]Bolton-Hunter Reagent. [$^{125}$I]IL-1β (17.5 ng/ml) was incubated with monoclonal antibody for 90 min. at 37° C. and 200 ul of the mixture was added to cultures of BALB/c 3T3 fibroblasts (1×) and the cells removed for gamma-counting. Data is presented in FIG. 3 and is expressed as the % of control (binding in the absence of antibody). ILB1-H5,▲; -H6, ●; -H21, ■; -H34, ○; and -H67, □.

EXAMPLE 4

Figure 4A:
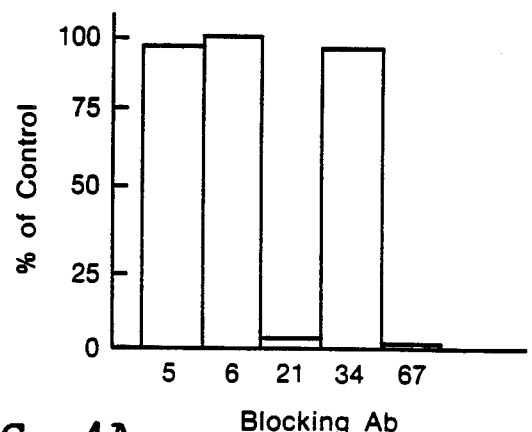
FIG. 4 shows that the inhibition of IL-1β activity results from the binding of the present antibodies to specific determinant sites on the IL-1β molecule and shows that two determinant sites which are on or close to the receptor binding site of IL-1β are involved.
Figure 4B:
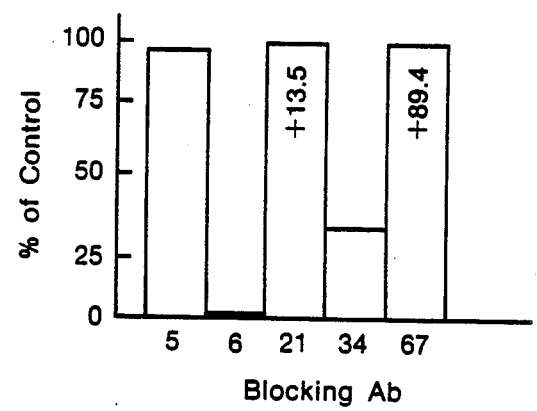

Monoclonal antibodies ILB1-H6 and -H34 identify one determinant site or epitope and ILB1-H21 and -H67 identify another determinant site or epitope involved in the biological activity of IL-1β. Monoclonal antibodies (5 μg/well) were tested for their ability to block the binding of monoclonal antibody biotin-conjungates (0.1 μg/well) to polyvinyl chloride microwells coated with a 0.2 μg/well solution of IL-1β. Binding of the antibody conjugate was detected by ELISA using strepavidin-peroxidase and orthophenylene diamine substrate solution. Data is presented in FIG. 4 and is expressed as the % of Control (Absorbance at 450 nm in the absence of blocking antibody). Positive values for blocking antibodies ILB1-H21 and -H67 versus the monoclonal antibody conjugate ILB1-H6 indicated binding greater than 100% of control.

EXAMPLE 5

Figure 5:
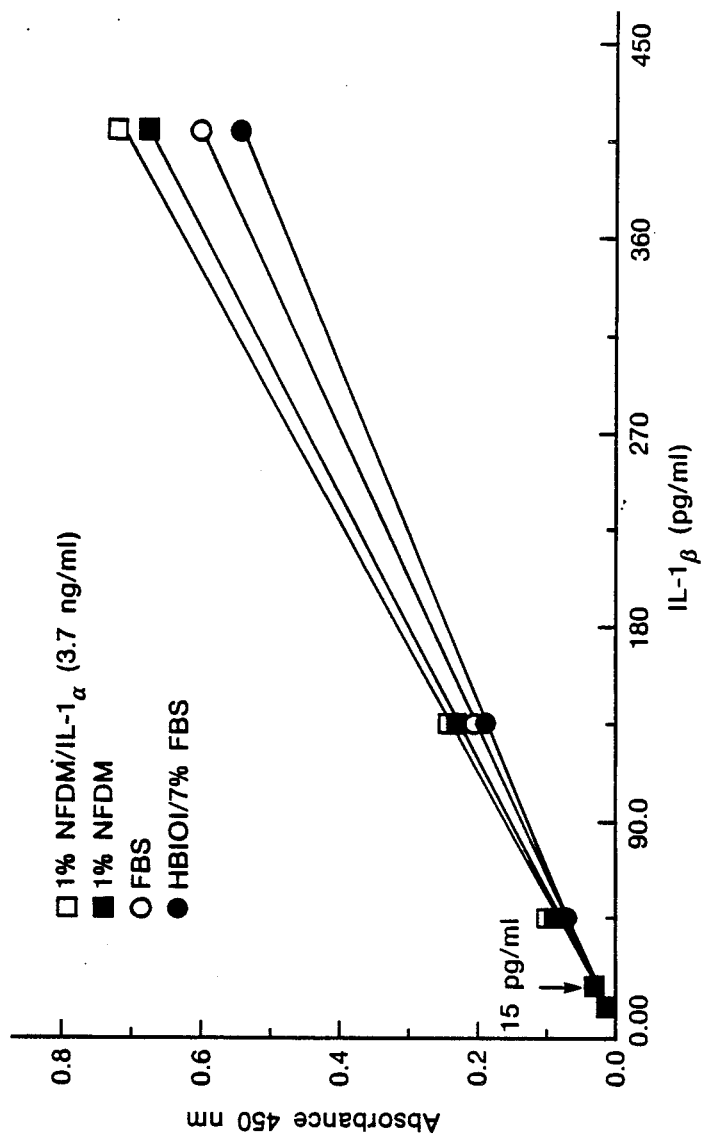
FIG. 5 shows that a two-site immunoassay enables precise and sensitive measurement of IL-1β activity.

A double determinant ELISA was conducted for IL-1β sensitive to 15 pg/ml. Monoclonal antibody ILB1-H6 (100 μl/well, 10 μg/ml) was coated on polyvinyl chloride microwells overnight at 4° C. The wells were countercoated with 5% non-fat dry milk (NFDM) phosphate buffered saline (PBS) for 1 hour at room temperature. 50 μl/well of IL-1β containing solution and 50 μl of biotinylated ILB1-H67 (2 μg/ml) were added in the diluents shown above and incubated for 2 hours at room temperature. After washing, 100 μl/well of streptavidin-peroxidase was added and the plate incubated for another hour. The wells were washed and incubated for 30 min. with 100 μl of orthophenylene diamine substrate solution. The results are summarized in FIG. 5.

EXAMPLE 6

Figure 6:
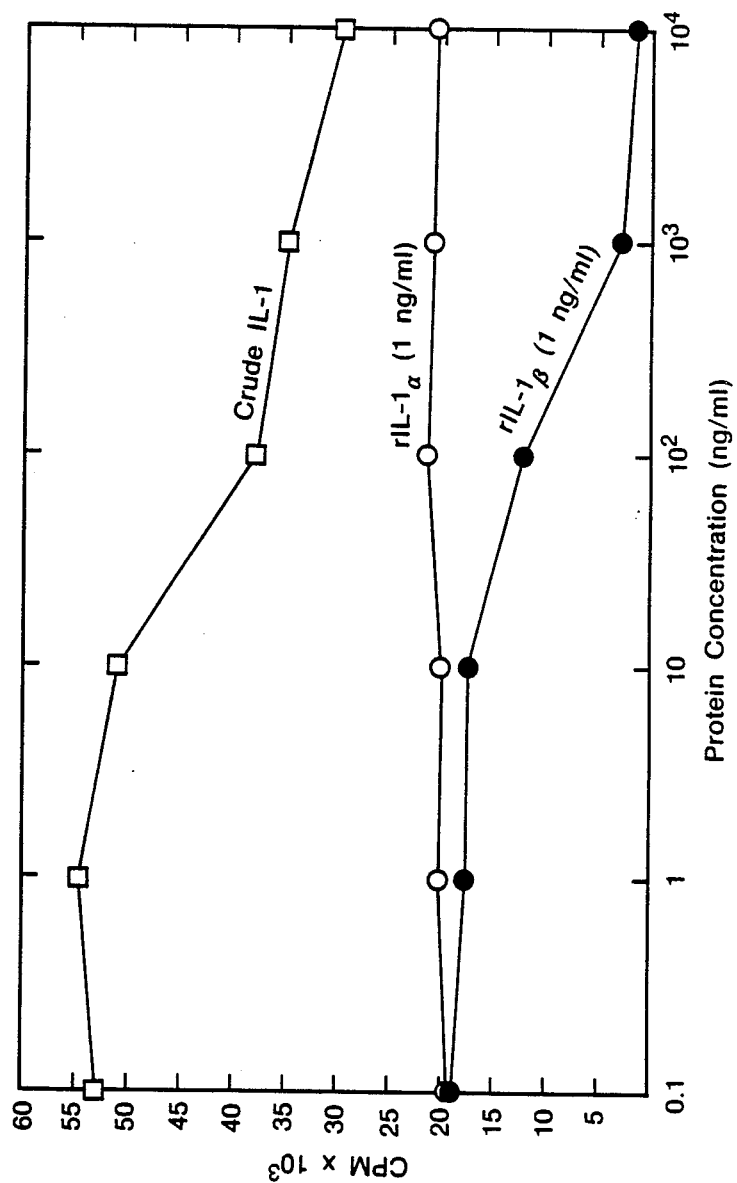
FIG. 6 shows that IL-1β blocking antibodies enable the distinction of IL-1β from other IL-1-like activities in biological assays.

Discrimination of IL-1β activity in a biological assay for Interleukins (IL-1s) was conducted. IL-1s were tested to a thymocyte proliferation asssay as described in Example 2. IL-1α (1 ng/ml), IL-1β (1 ng/ml), and IL-1 crude supernatant (1:20 dilution of supernatant from human adherent PBLs cultured with 20 μg/ml LPS for 24 hrs). The amount of ILB1-H67 added is shown on the x-axis of FIG. 6 vs. [$^3$H]thymidine incorporation on the y-axis.

EXAMPLE 7

Affinity constants were calculated using data obtained from an immunoprecipitation radioimmunoassay (RIA) of [$^{125}$I]IL-1β binding of different antibody concentrations as described above. The results are summarized in Table 1.

TABLE 1

| ANTIBODY AFFINITY OF IL-Iβ MONOCLONAL ANTIBODIES | |
|---|---|
| ANTIBODY | K (× 10$^9$ L/MOL) |
| H5 | .033 |
| H6 | 26 |
| H21 | 40 |
| H34 | 64 |

The invention has been described in detail with particular reference to the above embodiments. It will be understood, however, the variations and modifications can be effected within the spirit and scope of the invention.

What is claimed is:

1. An immunoassay method for the detection of Interleukin-1β which comprises:

contacting a sample suspected of containing Interleukin-1β with a monoclonal antibody that binds to Interleukin-1β and does not bind to Interleukin-1α; that blocks binding of Interleukin-1β to Interleukin-1 receptors; and, that binds to Interleukin-1β and blocks biological activity of Interleukin-1β, in order to form an immune complex; and determining the presence of said immune complex in order to detect Interleukin-1β in said sample.

2. The method of claim 1 wherein said monoclonal antibody is selected from the group of monoclonal antibodies obtained from the group consisting of hybrid continuous cell lines having identifying characteristics of ILB1-H6 (ATCC designation HB 102019), ILB1-H21 (ATCC designation HB 10220), ILB1-H34 (ATCC designation HB 10221) and ILB1-H67 (ATCC designation HB 10222).

3. The method of claim 1 wherein said monoclonal antibody is conjugated to a label.

4. The method of claim 1 wherein said sample is a body fluid selected from the group consisting of whole blood, lymphatic fluid, serum, plasma, saliva, and urine.

5. A monoclonal antibody that binds to Interleukin-1β and does not bind to Interleukin-1α; that blocks binding of Interleukin-1β to Interleukin-1 receptors; and, that binds to Interleukin-1β and blocks biological activity of Interleukin-1β.

6. The monoclonal antibody of claim 5 which is the antibody obtained from a hybrid continuous cell line having identifying characteristics of ILB1-H6 and ATCC designation HB 10219.

7. The monoclonal antibody of claim 5 which is the antibody obtained from a hybrid continuous cell line having identifying characteristics of ILB1-H21 and ATCC designation HB 10220.

8. The monoclonal antibody of claim 5 which is the antibody obtained from a hybrid continuous cell line having identifying characteristics of ILB1-H34 and ATCC designation HB 10221.

9. The monoclonal antibody of claim 5 which is the antibody obtained from a hybrid continuous cell line having identifying characteristics of ILB1-H67 and ATCC designation HB 10222.

10. The monoclonal antibody of claim 5 conjugated to a label.

11. The monoclonal antibody of claim 10 wherein said label is selected from the group consisting of enzymes, radioisotopes, particulate labels, chromogens, chemiluminescers, fluorescers, coenzymes, free radicals, and bacteriophages.

12. A hybrid continuous cell line having identifying characteristics of expressing the antibody of claim 5.

13. A hybrid continuous cell line selected from the group consisting of hybrid continuous cell lines having identifying characteristics of ILB1-H6 (ATCC designation HB 10219), ILB1-H21 (ATCC designation HB 10220), ILB1-H34 (ATCC designation HB 10221), ILB1-H67 (ATCC designation HB 10222).

14. A kit for use in an immunoassay comprising in one or more containers the monoclonal antibody of claim 5.

15. The kit of claim 14 wherein said monoclonal antibody is conjugated to a label.

16. The kit of claim 15 wherein said label is selected from the group consisting of enzymes, radioisotopes, particulate labels, chromogens, fluorescers, chemiluminescers, coenzymes, free radicals, and bacteriophages.

17. The kit of claim 14 wherein said monoclonal antibody is unlabeled and said kit further comprises a conjugate of a specific binding partner of said monoclonal antibody and a label capable of producing a detectable signal.

18. The kit of claim 14 wherein said monoclonal antibody is bound to a support.

* * * * *